United States Patent
Helle et al.

(10) Patent No.: US 9,694,202 B2
(45) Date of Patent: Jul. 4, 2017

(54) BRACHYTHERAPY TEMPLATE ADAPTOR

(75) Inventors: Kevin Helle, Bartlett, IL (US); Jay Reed, Elk Grove Village, IL (US)

(73) Assignee: GE HEALTHCARE, INC., Princeton, NJ (US)

( * ) Notice: Subject to any disclaimer, the term of this patent is extended or adjusted under 35 U.S.C. 154(b) by 13 days.

(21) Appl. No.: 13/581,391

(22) PCT Filed: Mar. 31, 2011

(86) PCT No.: PCT/US2011/030671
§ 371 (c)(1),
(2), (4) Date: Aug. 27, 2012

(87) PCT Pub. No.: WO2011/123605
PCT Pub. Date: Oct. 6, 2011

(65) Prior Publication Data
US 2013/0012757 A1    Jan. 10, 2013

Related U.S. Application Data

(60) Provisional application No. 61/319,629, filed on Mar. 31, 2010.

(51) Int. Cl.
*A61N 5/10* (2006.01)

(52) U.S. Cl.
CPC .... *A61N 5/1007* (2013.01); *A61N 2005/1012* (2013.01)

(58) Field of Classification Search
CPC .......... A61N 5/1007; A61N 2005/1012; A61N 5/10; A61N 5/1001; A61N 5/1002; A61N 5/1014; A61N 5/1015; A61N 5/1016; A61N 5/1027; A61N 5/1028; A61N 2005/1023; A61N 2005/1024; A61B 17/3403; A61B 2017/3411
USPC .................................. 600/1-8; 604/116, 117
See application file for complete search history.

(56) References Cited

U.S. PATENT DOCUMENTS

| | | | | |
|---|---|---|---|---|
| 4,998,912 A | * | 3/1991 | Scarbrough et al. | 600/6 |
| 6,036,632 A | * | 3/2000 | Whitmore et al. | 600/7 |
| 8,301,228 B2 | | 10/2012 | Kindlein et al. | |
| 2002/0156361 A1 | | 10/2002 | Popowski et al. | |
| 2004/0059177 A1 | * | 3/2004 | Baltas et al. | 600/3 |
| 2007/0276358 A1 | * | 11/2007 | Barzell | A61B 17/3403 606/1 |

FOREIGN PATENT DOCUMENTS

| | | |
|---|---|---|
| EP | 1374951 | 1/2004 |
| WO | 99/61104 | 12/1999 |

OTHER PUBLICATIONS

PCT/US2011/030671 ISRWO Dated Jun. 1, 2011.

* cited by examiner

*Primary Examiner* — Charles A Marmor, II
*Assistant Examiner* — Carrie R Dorna
(74) *Attorney, Agent, or Firm* — Grogan, Tuccillo & Vanderleeden, LLP

(57) ABSTRACT

A brachytherapy template adaptor for performing brachytherapy procedures using needles smaller in diameter than the template is designed to accommodate. Additionally, a kit for adapting a brachytherapy template is provided.

10 Claims, 5 Drawing Sheets

BRACHYTHERAPY TEMPLATE ADAPTOR

This application is a filing under 35 U.S.C. 371 of international application number PCT/US2011/030671, filed Mar. 31, 2011, which claims priority to U.S. application No. 61/319,629 filed Mar. 31, 2010, the entire disclosure of which is hereby incorporated by reference.

FIELD OF THE INVENTION

The present invention is directed to the field of brachytherapy equipment. More specifically, the present invention relates to a template adaptor for performing brachytherapy procedures using needles smaller in diameter than the template is designed to accommodate.

BACKGROUND OF THE INVENTION

When performing a brachytherapy procedure, a physician or technician often must design and assemble the load pattern of radioactive brachytherapy seeds to be implanted into the body. With reference to FIG. 1, a perineal template 1 is supported on a patient stabilizing fixture 2 adjacent to a patient 3 in a manner to minimize any relative displacement between the template 1 and the patient 3. The template 1 includes an array of through-passages, where the passages arranged in a known grid pattern. The physician, knowing the location and size of the target tissue to be treated, will design the dose plan, ie, the three-dimensional array of brachytherapy seeds which will be implanted within and about the target tissue.

During implantation of seeds, perineal template 1 is utilized to direct the implant needles 4 into the prostate according to the dose plan. The template 1 utilizes a standard X-Y coordinate system. The template 1 also provides accurate guidance of the implant needle 4 through the template 1, providing penetration into the patient perpendicular to the template. The standard seed utilizes an 18 gauge implant needle, which requires a template for this specific sized needle. Although the X-Y coordinate system is common among different manufacturers of templates (labelling may be slightly different) the mechanism for attachment to the stabilizing table can vary greatly. There are currently dozens of different perineal templates on the market, each tailored to different attachment mechanisms (or "leg designs").

Thus, there are numerous perineal template designs on the market, each employing a particular design for its array of through passages and accommodating a particular leg design. For example, the template designs may consist of a standard X-Y hole pattern, an alpha numeric identification system for the X-Y coordinates (unique to the dose planning system used), or a unique profile at the bottom of the template to accommodate different ultrasound probe designs. The leg designs can vary to accommodate the different stepper stabilizer models, which can dictate different distances between the legs, and different leg diameters, or incorporate adjustable collars on the legs to allow for positioning of the grid based upon different stepper stabilizers. There are also a number of different adaptors that allow for connecting one style of template to a specific style of stepper stabilizers.

Finally, there are numerous dose planning software packages specific to available implant templates. These software packages will provide specific dose profiles by directing that a needle with a particular brachytherapy load be inserted into an identified through-passageway. As different templates employ different schemes for labeling the rows and columns of their through-passageways, the dose planning software takes this into account when presenting the dose plan.

A new smaller diameter seed has been designed that utilizes a smaller diameter 20-gauge needle to implant the seeds. A perineal template that has smaller diameter passageways is required for accurate placement of needles and seeds. Initial implants were supported by replicating the template being used at a specific clinic with a 20 gauge version, at a great expense.

With the market opening on the smaller diameter seed (and thus smaller needle) a more cost efficient method of supporting the surgical implant is needed.

A 20-gauge template is required as the thinner diameter of the 20-gauge needles results in a standard 18-gauge template having through-passages which are too large in diameter for ensuring proper placement of a 20-gauge needle. That is, the longitudinal axis of the 20-gauge needle will be positioned off-axis of the longitudinal axis of the 18-gauge needle passageway of the template. An off-axis needle will result in, brachytherapy seeds being delivered in deviation of the dose plan.

It has thus far been very difficult, and not cost effective, to establish the correct style needed for each new user site that wants to switch to smaller diameter seeds (and thus needles). In some cases the only option would be to create a unique perineal template to accommodate a particular site. This has been done at a cost well in excess of $1000 per template. Often, several templates are needed per user site, further complicating and increasing the expense of providing a new line of perineal templates for the new smaller-diameter seeds.

Therefore, given the ubiquity of templates sized for accommodating 18-gauge needles, and the cost involved in providing a templates for 20-gauge needles for all of the available leg designs, there is a need in the art for a simple device for ensuring the proper centering of a brachytherapy needle within the through-passages of the existing templates.

SUMMARY OF THE INVENTION

In view of the needs of the prior art, the present invention provides a template adaptor which can be used with the existing template hardware for performing brachytherapy procedures using needles smaller in diameter than the template is designed to accommodate. For example, where there is an existing supply of brachytherapy templates designed to accommodate 18-gauge brachytherapy needles, the template adaptor of the present invention can attach to the 18-gauge template and provide an array of 20-gauge through passages in registry with the 18-gauge through passages of the existing template. Desirably, each of the 20-gauge through passages provided by the template adaptor of the present invention are co-axially aligned with an 18-gauge through passage of the prior art template.

The brachytherapy template adaptor of the present invention includes a brachytherapy template adaptor body defining a plurality of adaptor through-passages arrayed to be positioned in unique fluid registry with a plurality of through-passages defined by a brachytherapy template, wherein at least a portion of the adaptor through-passages having a smaller transverse span than the through-passages of the brachytherapy template. Desirably, the through passages of the present invention are defined by a chamfer surface which transitions from a larger diameter opening defined by a first major surface of the adaptor to the smaller diameter span of the through passage of the adaptor body. The chamfer surface may have a frustroconical shape or have the shape of a rounded annular rim.

DETAILED DESCRIPTION OF THE PREFERRED EMBODIMENT

Figure 1:
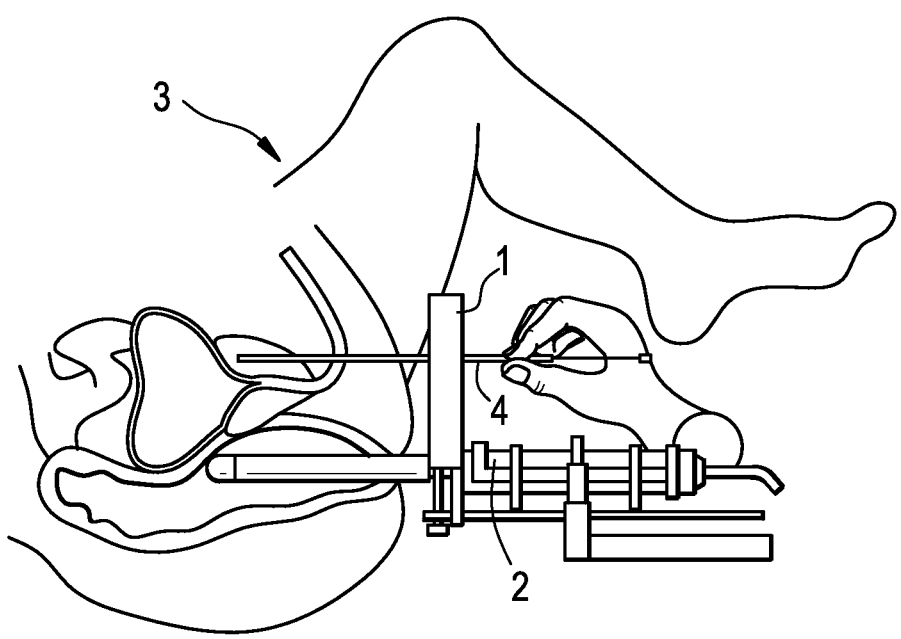
FIG. 1 depicts a brachytherapy procedure of the prior art.

To address the template issue, a template adapter has been designed and developed to allow the current users of 18 gauge standard seed templates to implant, with the required accuracy and tolerances, a 20 gauge needle. The template adapter mechanically fits onto the back of the 18 gauge needle template. The adapter mirrors the X-Y coordinate system of the existing 18 gauge template, yet has a leading chamfer and appropriately sized through passageways for the 20 gauge needle. The adapter fits into the available area between the back of the current template (towards the patient) and the patient's perineum. The added overall thickness does not affect dose planning or the ability to extend the needle into the patient because it fits into a current void in the clinical implantation of the radioactive seeds. Since only the X-Y coordinate system, and mechanical fastening pins, is needed the template can be manufactured at approximately ⅕ of the cost of a current template. In addition, no labelling is needed for the coordinate system since the reference the physician will be using is on the existing 18 gauge front needle template.

The present invention also provides cost efficiencies to set up new users to the next generation of seeds. This cost savings is greatest when multiple templates are needed for surgical efficiencies (sterilization, preparation, etc.). A physician may likely prefer to be able to change from a larger to smaller sized seed quickly and efficiently. This is most important when a physician is only trying the new and smaller seed/needle since not every physician would opt for the new smaller diameter seed until more publications are generated stating the clinical advantages of the newer sized seed.

The present invention is therefore cost-effective from a manufacturing perspective, as only manufacturing the new template adaptor is required in order to support the new seed technology.

The present invention is also "Green" in approach, as there are thousands of the current (larger) templates in use. All of these templates may continue to be used with the present invention while the physicians adopt a new treatment approach of employing the smaller diameter seed and needle that the existing templates could not properly accommodate.

The template adapter is designed to only replicate the X-Y portion of the implant grid, and small probe cut-out (ultrasound probe used for seed Z axis positioning. The adapter desirably uses the 4 corner holes of the X-Y grid (not utilized during seed implants) to mechanically lock onto the existing template with a tight tolerance fit. The adapter had chamfers to easily allow the passage of the X-Y controlled needle into the adapter, then reduces to the through passage sized to optimally guide the needle into the patient. It should be noted that the chamfer and through passage of the adapter is proportionately equivalent to the existing template (reduced proportionately to the smaller diameter needle). The adapter can be placed onto the existing template per or post sterilization depending on test factors determined after the adapters are manufactured (there will be numerous tests to confirm correct sized chamfers, holes, guide pins, probe cut-outs, etc. are used). There will be a full documentation package to explain how to set up and use the adapter with existing templates, dose planning software, surgical preparation, etc. The adapter will only be labelled on the top to clearly identify it as an adapter for 18 to 20 gauge use. The adapter will have finger holds designed into the sides for easy removal if needed for sterilization or needle use change.

It is possible that the adapter may be made ¼ or ½ inch thick, or approximately 0.800 inches thick, but it is thought that much less vertical guidance will be needed since the needle is held much more captive by the existing template than the current template is held before needle introduction. The adapter will be made, most likely, out of anodized aluminum (such as 6061-T6), which is comparable to most templates. Some templates are made from plastic, however the re-usable and re-sterilizable versions are mostly made of aluminum finish treated in this manner. Other final design decisions for the adapter may be driven by the particular procedure or other supporting equipment to be used.

Figure 2:
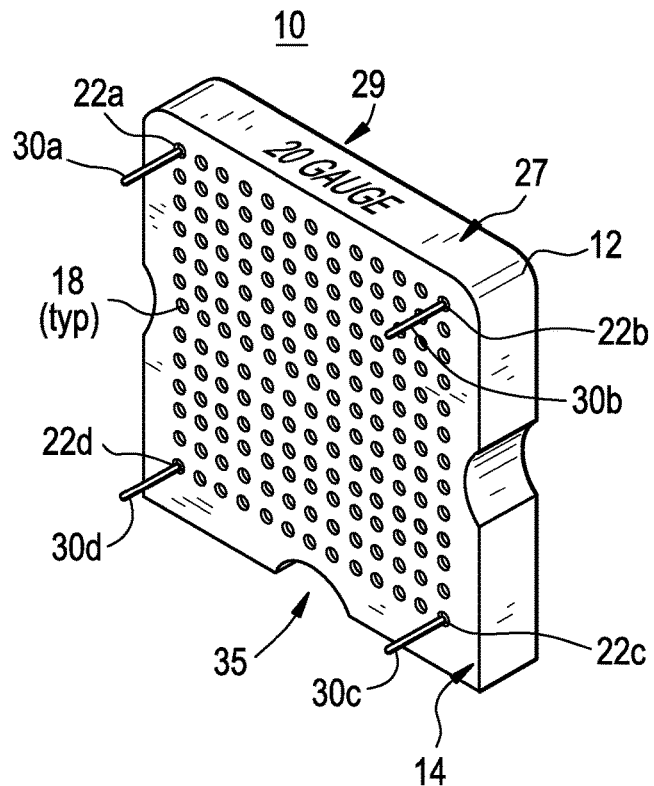
FIG. 2 is an oblique view of a template adaptor of the present invention.
Figure 3:
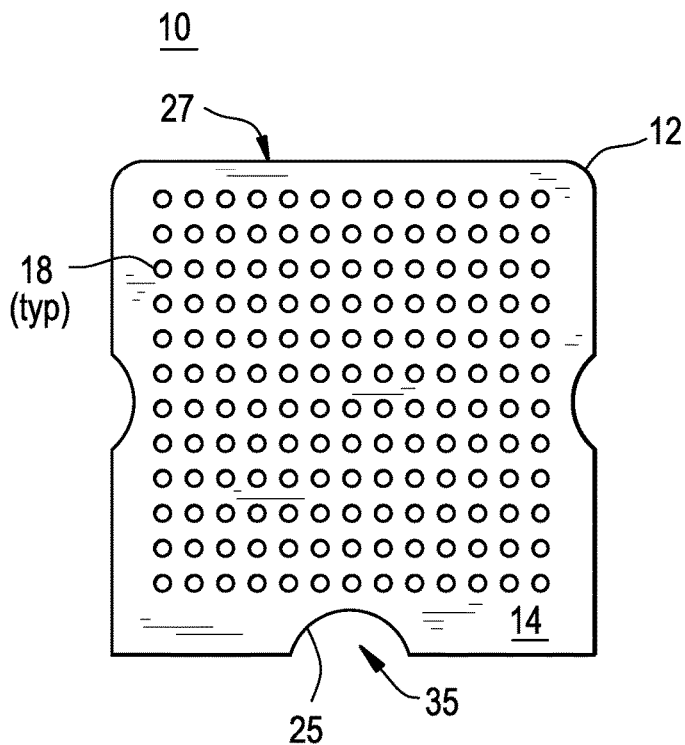
FIG. 3 depicts a front elevational view of the template adaptor of FIG. 2.
Figure 4:
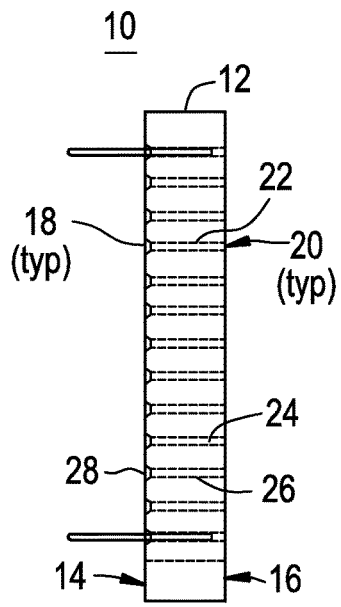
FIG. 4 depicts a side elevational view of the template adaptor of FIG. 2.

Referring now to FIGS. 2-4, the present invention provides a template adaptor 10, having an adaptor body 12. Body 12 includes opposed planar major surfaces 14 and 16. First major surface 14 defines a number of inlet openings 18, Second major surface 16 defines an equal number of perineal openings 20, and body 12 defines an equal number of elongate through passageways 22 extending in fluid communication between associated inlet and perineal openings. Each through passageway 22 is further defined by an elongate passageway wall 24. Each passageway wall 24 is desirably defined by an elongate cylindrical surface 26 and a chamfer surface 28. Chamfer surface 28 extends from first major surface 14 to cylindrical surface 26, while cylindrical surface 26 extends from chamber surface 28 to second major surface 16.

Chamfer surface 28 is shown to have a frustroconical shape which tapers from a first diameter, at inlet opening 18, to a second smaller diameter where it meets cylindrical surface 26. Chamfer surface 28 therefore provides a transition from the larger diameter through passageways of template 1, to the smaller diameter through passageway 22 of the present invention.

Template adaptor 10 desirably provides a two-dimensional 13×13 array of through passageways 22, corresponding to a similar 13×13 array of through passageways of template 1. Regardless of the actual number provided, each of the through passageways 22 of template adaptor 10 are desirably provided to be co-axially aligned with a unique through passageway of the larger template 1, although the present invention contemplates that the template simply provide a known alignment between each of its through-passages with respective through-passage of the larger template 1 so that dose planning may be properly completed. In this manner, template adaptor 10 may be used with the dose planning software provided for template 1. Additionally, adaptor body 12 may be shaped to accommodate other instrumentation used during a brachytherapy procedure. For example, in adaptor body 12 is shown as having an arcuate bottom edge 25 so as to define a notch 35 which accommodates an ultrasound probe used in conjunction with a mating set of legs. Additionally, it is contemplated that adaptor body 12 includes a planar upper edge 27 on which indicia 29 may be provided so as to indicate the needle gauge size the template adaptor is sized to accommodate.

While the present invention contemplates that adaptor body may have any thickness, adaptor body 12 desirably has a thickness (as measured by the length of through-passageway 22) that will maintain the needle aspect ratio and thus help direct the needle straight during patient insertion. For example, the thicker adaptor body 12 is, and thus the longer that cylindrical surface 26 slidingly engages the needle, the better the adaptor's ability to properly guide the needle. Thus, the needle aspect ratio (ie, the length of surface 26 to the diameter of passageway 22 it defines) is desirably at least 3, and more desirably at least 5.

Figure 5:
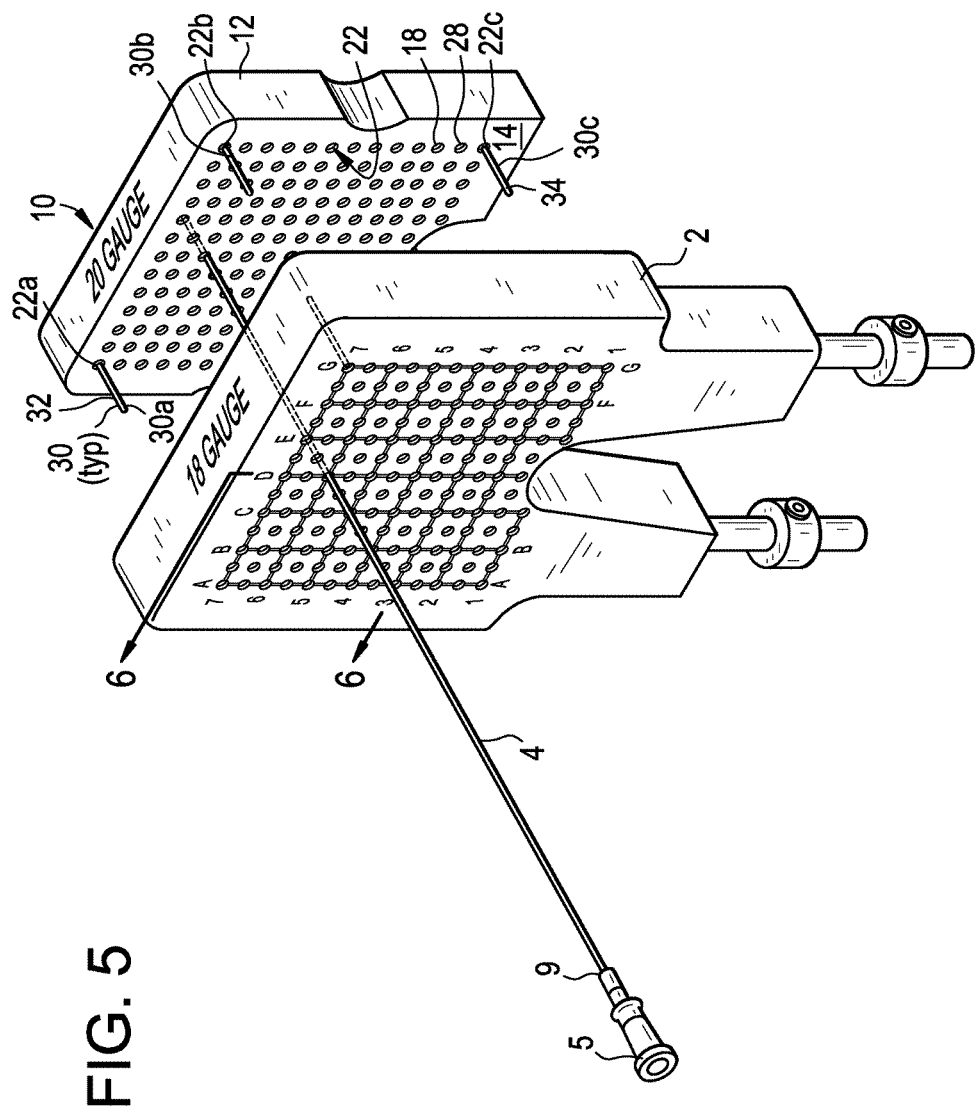
FIG. 5 is an exploded assembly view of an adaptor template of the present invention and a template of the prior art, showing a brachytherapy needle being extendable through aligned through passages of the two template bodies.
Figure 6:
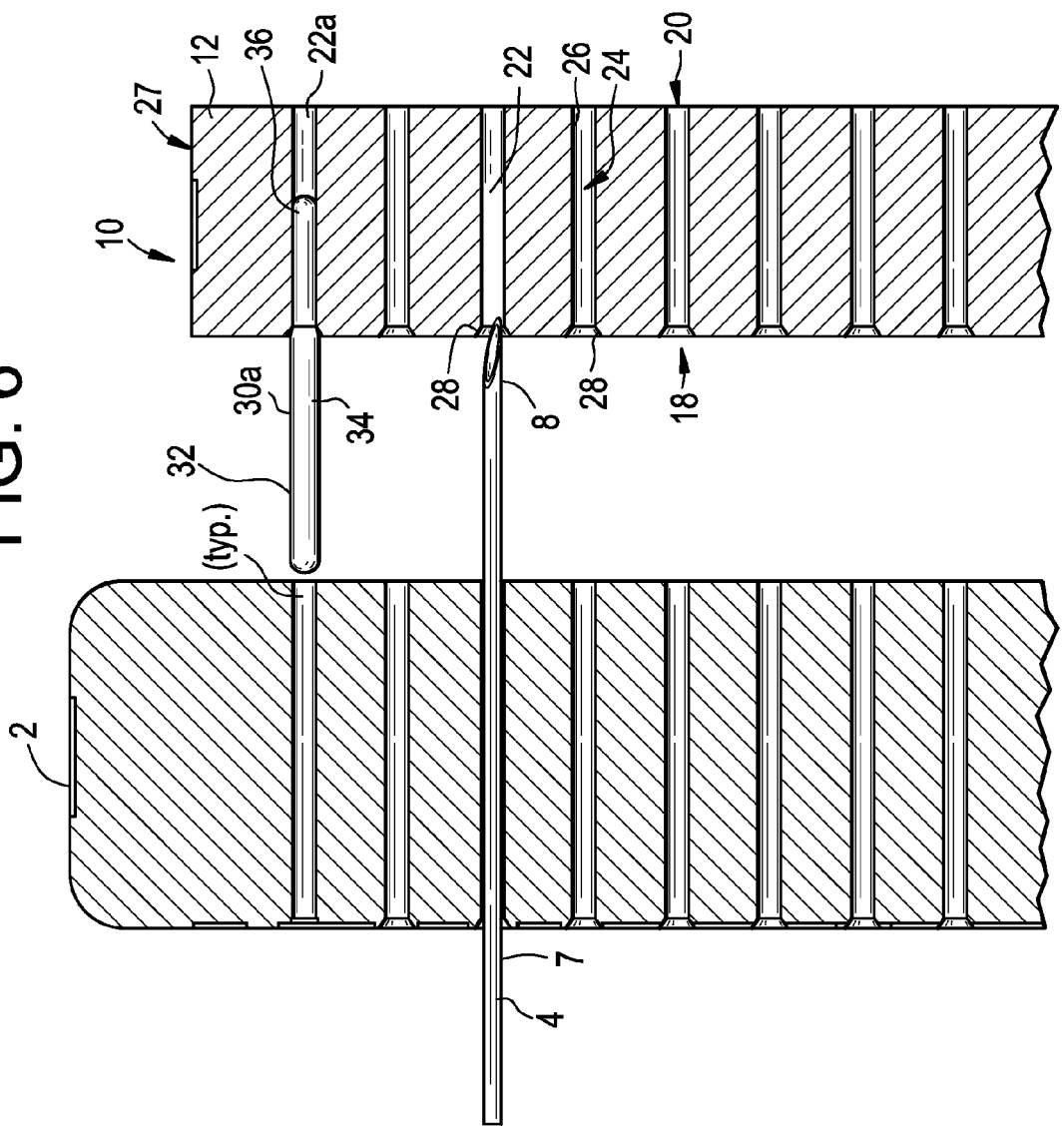
FIG. 6 is a partial cross-sectional view of the assembly view of FIG. 5, depicting a brachytherapy needle being accommodated by the two template bodies.

With additional reference to FIGS. 5 and 6, template adaptor 10 is desirably attached to template 1 by grid pins 30. Each grid pin 30 includes an elongate pin body 32, having a first portion 34 sized to be held in the passageways 6 of template 1, and a second portion 36 sized to be held in passageways 22 of template adaptor 10. For example, first portion 34 may have the outer diameter of an 18-gauge needle and second portion 36 may have the outer diameter of a 20-gauge needle. The sizing tolerances provide a snug fit so that the pin portions may be inserted into and withdrawn from their respective passageways while also holding the two templates such that their respective through passageways are in co-axial alignment. Desirably, four such grid pins 30a-d are employed, one in each of the four outermost corner passageways 22a-d of the grid array. The present invention further contemplates that fewer guide pins, although desirably at least two or at least three, may be employed. Additionally, the present invention contemplates that other means of holding the templates together in the disclosed proper orientation may also be employed. Furthermore, while template adaptor 10 is desirably remove ably attached to template 1 so as to allow sterilization of the component parts between clinical usages, the present invention further contemplates that adaptor 10 may be permanently adhered or affixed to template 1.

The present invention further contemplates that other means of securing template adaptor 10 and a template together may be employed. For purposes of illustration and not of limitation, the adaptor body of a template adaptor of the present invention may include prongs which grip template 1 at one or more locations about its perimetrical edge. Such prongs are contemplated to grip the template about its perimetrical edge, or could also extend thereabout and grip the opposing face of the template than that which the template adaptor is held against. Alternatively, the template adaptor and template may be adhered to one another by an acceptable adhesive. It is also contemplated that the template adaptor and template may be held together by conventional fasteners such as screws, nails, or clips, and the like. Alternatively still, the means for securing the template adaptor and template together may space the two apart (while still providing registry between the through-passageways of the template adaptor with those of the template). A key consideration for the means by which a template adaptor of the present invention is secured to a template is that each of the through-passages of the template adaptor to be utilized in a brachytherapy implantation procedure are in registry with a through-passageway of the template.

With additional reference to FIGS. 5 and 6, brachytherapy needle 4 is contemplated as being a 20-gauge needle, although it is clear that the teachings of the present invention may be used for a brachytherapy needle of any size when working with a template that is too large for the implant needle. Needle 4 includes an elongate tubular needle body 7 defining opposed sharp and working open ends, 8 and 9 respectively. Needle 4 is desirably preloaded with a brachytherapy member within. The brachytherapy member may take the form of a brachytherapy strand or a train of brachytherapy seeds and/or spacers. A brachytherapy strand includes one or more brachytherapy seeds and/or spacers within a biocompatible carrier material. Each needle 4, furthermore, desirably includes a luer hub 5 supported at working end 9, for ease of handling the needle.

Figure 7:
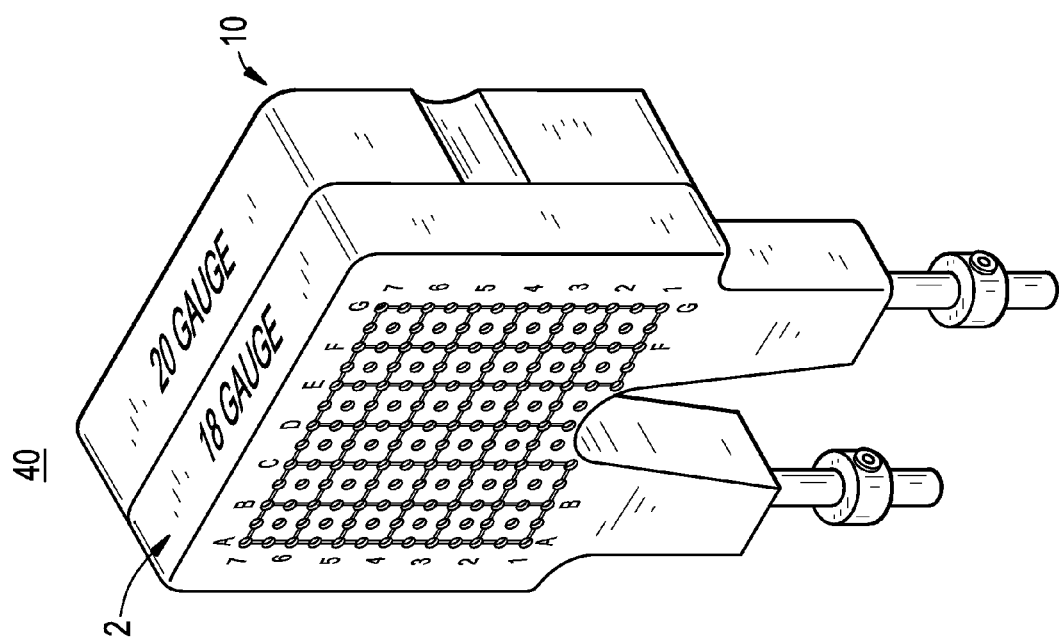
FIG. 7 depicts a template of the prior art having a template adaptor of FIG. 2 attached thereto.

FIG. 7 depicts an assembly 40 composed of template adaptor 10 attached to template 1. Assembly 40 employs guide pins 30 (not shown) for properly aligning and holding template adaptor 10 to template 1.

While template adaptor 10 has, thus far, been shown to attach to the rear surface of template 1, i.e., so as to be mounted between template 1 and the patient, the present invention further contemplates that template adaptor 10 may be mounted to the front surface of template 1, i.e., so as to be mounted on the opposing surface of template 1. When mounted on the front surface of template 1, the present invention contemplates that the perimetrical edge of adaptor 10 may fit within the indicia on the front face of template 1 (marking the columns and rows) so that the placement of the needles will correspond to the markings on the template. Alternatively, the present invention also contemplates that template adaptor 10 may extend over and cover the front surface indicia of template 1, in which case template adaptor 10 will provide front surface indicia corresponding to the template and the dose plan.

The present invention further provides a kit for adapting a brachytherapy template comprising a plurality of guide pins 30 and a template adaptor 10, wherein template adaptor 10 is adapted for use with the brachytherapy template and provides a through passageway having a smaller diameter than a corresponding through passageway of the brachytherapy template.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A brachytherapy template adaptor for a brachytherapy template comprising:
   a brachytherapy template adaptor body defining a plurality of adaptor through-passages arrayed to be positioned in unique fluid registry with a plurality of through-passages defined by a brachytherapy template, at least a portion of the adaptor through-passages having a smaller transverse span than the through-passages of the brachytherapy template;
said adaptor through-passages are defined by a chamfer surface and an elongated cylindrical surface, wherein the chamfer surface transitions from a larger diameter opening defined by a first major surface of the adaptor to a smaller diameter span of the adaptor through-passage, and wherein the elongated cylindrical surface is defined by the small diameter span and extends from the chamfer surface to a second major surface of the adaptor.

2. A brachytherapy template adaptor of claim 1, wherein each said adaptor through-passage includes an elongate central axis, wherein the spacing of each central axis is according to the spacing array of the brachytherapy template.

3. A brachytherapy template adaptor of claim 1, wherein the chamfer surface has a frustroconical shape.

4. A brachytherapy template adaptor of claim 1, further comprising an attachment mechanism for holding said adaptor body with respect to the brachytherapy template.

5. A brachytherapy template adaptor of claim 4, wherein said attachment mechanism further comprises at least one elongate locating pin extending from an adaptor through-passage, said locating pin including a free end to be received in a corresponding through-passage of the brachytherapy template.

6. A brachytherapy template adaptor of claim 4, wherein said attachment mechanism further comprises a transverse wall for engaging the body of the brachytherapy template.

7. A kit for a brachytherapy template comprising:
a brachytherapy template adaptor of claim 1; and
a plurality of guide pins adapted to hold said template adaptor to said template so that each said through-passage of said template adaptor extends in fluid communication with a through-passage of said template passage.

8. A kit of claim 7, wherein said guide pins are adapted to hold said template adaptor to said template so that each said through-passage of said template adaptor is co-axially aligned with a through-passage of said template.

9. A kit of claim 7, wherein said guide pins include a first portion having an outer diameter corresponding to a through-passage of the template and a second portion having an outer diameter corresponding to the diameter of a through-passage of the template adaptor.

10. A brachytherapy template and a brachytherapy template adaptor mountable to the brachytherapy template, the template and adaptor comprising:
a brachytherapy template adaptor body defining a plurality of adaptor through-passages arrayed to be positioned in unique fluid registry with a plurality of through-passages defined by the brachytherapy template, at least a portion of the adaptor through-passages having a smaller transverse span than the through-passages of the brachytherapy template, the transverse span of the through-passages of the brachytherapy template corresponding to a first diameter of a first needle, and the transverse span of the adapter through-passages corresponding to a second diameter of a second needle, the second diameter being smaller than the first diameter;
said adaptor through-passages are defined by a chamfer surface and an elongated cylindrical surface, wherein the chamfer surface transitions from a larger diameter opening defined by a first major surface of the adaptor to a smaller diameter span of the adaptor through-passage, wherein the elongated cylindrical surface is defined by the smaller diameter span and extends from the chamfer surface to a second major surface of the adaptor.

* * * * *